United States Patent [19]

Crawford

[11] 4,250,168

[45] Feb. 10, 1981

[54] COLD SORE TREATMENT METHOD

[76] Inventor: Horace R. Crawford, 7227 Oakbluff, Dallas, Tex. 75240

[21] Appl. No.: 57,396

[22] Filed: Jul. 13, 1979

[51] Int. Cl.³ .................... A61K 33/10; A61K 33/00; A61K 33/02

[52] U.S. Cl. .................................. 424/127; 424/156; 424/166

[58] Field of Search ........................ 424/127, 166, 156

[56] References Cited

PUBLICATIONS

*The Merck Index,* 12th Ed., (1972), pp. 982 & 983, Merck & Co., Inc., Rahway, N. J.

*Primary Examiner*—Frederick E. Waddell
*Attorney, Agent, or Firm*—Richards, Harris & Medlock

[57] ABSTRACT

A method is provided for treating cold sores in which a carbonate salt is orally ingested, thereby eliminating soreness caused by the cold sore and curing the cold sore. According to the invention, the preferred carbonate salt is sodium bicarbonate and it is preferably ingested in dosages of from about 200 milligrams to about 4 grams, the dosage being repeated about every four to twelve hours and continued for a period up to about four days. The carbonate salt may be ingested by any suitable manner such as tablet, capsule, powder or in an aqueous solution.

8 Claims, No Drawings

COLD SORE TREATMENT METHOD

TECHNICAL FIELD

This invention relates to treatment of cold sores or fever blisters.

BACKGROUND ART

Fever blisters or cold sores are generally believed to be caused by a certain type of the herpes simplex virus. This type of virus usually affects the mouth, causing recurrent sores on the lips and areas around and in the mouth. On occasion, this virus gets into the blood stream and causes a serious infection in babies.

In addition to their unattractive appearance, recurrent fever blisters may burn and be quite sore. There is also some danger of secondary bacterial infection in the open ulcer.

It is possible to use local anesthetics to mitigate pain, antibiotics to control secondary bacterial infections when they occur and ointments to soften crusts. However, use of an antibotic frequently causes side reactions and tends to sensitize the patient to further effective or safe use of the drug. Hence it is important to avoid the secondary infection stage. Until the present invention, it is not believed that an effective cure has been available. Moreover, the present invention also works to alleviate discomfort from the pain associated with fever blisters.

A need has thus arisen for an effective method of treating fever blisters or cold sores.

DISCLOSURE OF INVENTION

According to the present invention, a novel method is provided for treating fever blisters or cold sores which comprises orally ingesting an effective amount of a carbonate salt. The effect of the carbonate salt on the cold sore is to progressively reduce and eliminate soreness caused by the cold sore, reduce the amount of fluid contained in the sore and cause the sore to heal, usually within several days and sometimes within less than one day.

While carbonate salts such as calcium carbonate and potassium bicarbonate can be utilized according to the invention, sodium bicarbonate is the preferred chemical utilized according to the method of the present invention.

DETAILED DESCRIPTION

Cold sores or fever blisters, are commonly believed to be a human virus disease caused by a herpes simplex virus and characterized by a blister or groups of blisters containing a clear fluid formed on the skin or mucous membranes such as the lips or mouth. In addition, the cold sores or fever blisters may be often accompanied by a cold or fever or both. The blister associated with this disease may cover a large portion of a lip and cause severe itching, stinging and localized pain. Cold sores are often unsightly or unbecoming to the owner. Without medication it is not uncommon for a blister to remain on the skin in excess of one week and take two weeks to completely heal, and in some instances where secondary infections occur the healing period can be even further prolonged.

As used herein, "cold sore" is the equivalent of "fever blister."

Ingesting quantities of carbonate salts, preferably at spaced apart intervals for several days, will cure a cold sore or fever blister and also reduce the pain, itching, stinging and swelling associated with the blister.

As used in this disclosure, "carbonate salt" includes carbonate, such as calcium carbonate, for example, and bicarbonate, such as sodium bicarbonate, for example. According to the invention, the carbonate salts which may be used include, for example, sodium bicarbonate, potassium bicarbonate, calcium carbonate, aluminum carbonate and ammonium carbonate or combinations thereof.

The preferred carbonate salt according to the invention is sodium bicarbonate, commonly known as baking soda. Generally, the effective dosage of sodium bicarbonate is in the range of from about 200 milligrams to about 16 grams on a daily basis. It is preferred that the total daily dosage be ingested over the course of the day in discrete doses taken from about every four to twelve hours. Preferably, the dosage of sodium bicarbonate ranges between about 200 milligrams to about 4 grams taken about every six hours. Similar dosages are also used when using calcium carbonate or potassium bicarbonate. The carbonate salt may be taken in any standard form, such as in tablet, capsule or powder form or as an aqueous solution.

The practice of the method of the present invention provides an effective treatment for cold sores or fever blisters during any stage of the disease.

EXAMPLE 1

The human subject noticed a fever blister starting on her lower left lip and was given approximately 4 grams of sodium bicarbonate for oral ingestion. Within 24 hours thereafter, the soreness was essentially eliminated.

EXAMPLE 2

The human subject noticed a fever blister forming on her upper lip and orally ingested approximately 3.5 grams of sodium bicarbonate in water and repeated the dosage about every four to six hours for two days. On the third day the dosage was reduced to about 3.5 grams of sodium bicarbonate every six to eight hours and on the fourth day the subject orally ingested approximately 3.5 grams of sodium bicarbonate once. By the end of the fifth day, the fever blister had dried up completely.

EXAMPLE 3

The subject complained of a newly developing fever blister. Approximately 2 grams of sodium bicarbonate was orally ingested and the dosage was repeated about 45 minutes later. There was no discomfort or symptoms from the fever blister after taking the second dose of sodium bicarbonate.

EXAMPLE 4

The subject noticed a small bump on his upper right lip during the first day. By the second day the bump had developed into a robust fever blister on subject's upper right lip, approximately 0.5 centimeters in diameter. The subject ingested 8 grams of calcium carbonate over a period of approximately 16 hours in the form of 500 milligram tablets. After 16 hours from the first dose, the blister was essentially gone with a slight tenderness of the tissue remaining. After approximately 24 hours from the first dose of calcium carbonate, soreness caused by the fever blister was eliminated and the blister was essentially cured.

While this invention has been described in relation to its preferred embodiments, it is to be understood that various modifications thereof will now be apparent to one skilled in the art upon reading the specification, and it is intended to cover such modifications as fall within the scope of the appended claims.

I claim:

1. A method of treating cold sores which comprises orally ingesting an effective amount of a carbonate salt to cure said cold sore and eliminate soreness caused by said cold sore.

2. The method as described in claim 1 wherein the carbonate salt is sodium bicarbonate.

3. The method as recited in claim 2 wherein the dosage of sodium bicarbonate is from about 200 milligrams to about 4 grams.

4. The method as recited in claim 3 wherein the dosage is repeated about every four to six hours.

5. The method as recited in claim 3 wherein the dosage is repeated about every six to twelve hours.

6. The method as recited in claim 5 wherein the dosage is continued for a period of about four days.

7. The method as recited in claim 1 wherein said carbonate salt is selected from the group consisting of potassium bicarbonate, calcium carbonate, ammonium bicarbonate, and aluminum carbonate.

8. The method as recited in claims 2, 6 or 7 wherein the total daily dosage is from about 200 milligrams to about 16 grams.

* * * * *